United States Patent [19]
Tipton et al.

[11] 3,959,788
[45] May 25, 1976

[54] IONIZATION-TYPE FIRE DETECTOR

[75] Inventors: William C. Tipton, Newark; Michael Suchomel, Mountainside; John Z. Taran, Morristown, all of N.J.

[73] Assignee: General Signal Corporation, Rochester, N.Y.

[22] Filed: May 10, 1974

[21] Appl. No.: 468,950

[52] U.S. Cl. .............................. 340/237 S; 250/381
[51] Int. Cl.² .................... G08B 17/10; H01J 39/28
[58] Field of Search ................ 340/237 S; 250/381, 250/382, 384, 385, 390, 239, 574

[56] References Cited
UNITED STATES PATENTS

| | | | |
|---|---|---|---|
| 3,460,124 | 8/1969 | Smith et al. | 340/237 S |
| 3,594,751 | 7/1971 | Ogden et al. | 340/249 X |
| 3,681,603 | 8/1972 | Scheidweiler et al. | 340/237 S X |
| 3,731,093 | 5/1973 | Scheidweiler et al. | 340/237 S X |

*Primary Examiner*—John W. Caldwell
*Assistant Examiner*—Daniel Myer
*Attorney, Agent, or Firm*—Pollock, Vande Sande & Priddy

[57] ABSTRACT

An ionization-type fire detector having a pair of ionized chambers, one of which is arranged so that products of combustion can flow therethrough while the other is substantially isolated from the products of combustion. As a result, when combustion products are present, the electrical conductivity in one chamber is different than the other, and this condition is sensed to provide a fire alarm signal. The first-mentioned ionized chamber is defined by inner and outer shells of plastic material which are suitably spaced from each other and with the inner surface of the outer shell being provided with a conductive coating. The spaced plastic surfaces are curved, and one of the shells defines a cavity which forms at least a part of said first-mentioned chamber. It has been found that this minimizes the adverse effects caused by wind drafts which otherwise can affect the electrical conductivity in the first chamber and provide an erroneous fire alarm signal. The overall arrangement of the detector is such as to provide a compact unit which is attractive in appearance and relatively low cost to manufacture.

16 Claims, 8 Drawing Figures

IONIZATION-TYPE FIRE DETECTOR

BACKGROUND OF THE INVENTION

Ionization-type fire detectors are well known in the art. It is common in such detectors to provide a pair of ionization chambers which are constantly maintained ionized by a source of radiation. One of the chambers is so arranged that the products of combustion can enter therein and thus affect the electrical conductivity in the chamber, whereas the other chamber is generally substantially isolated from the products of combustion and thus has its conductivity affected only negligibly, if at all, thereby. An electronic bridge and amplifier circuit responds to the conductivity levels in the two separate chambers and senses their difference in conductivity when combustion products enter the first chamber, being then effective to provide a distinctive alarm signal.

One of the disadvantages of the prior art ionization-type fire detectors is that they are generally quite bulky and decidedly unattractive in appearance. Another drawback is their considerable susceptibility to drafts of wind. More particularly, it has been found that a draft of wind or strong air current passing through the first-mentioned ionization chamber tends to affect the electrical conductivity of that chamber in much the same way that occurs when products of combustion enter the chamber, and it may thus occur therefore that a false fire alarm signal may be given when such wind drafts or air currents are present.

SUMMARY OF THE INVENTION

It is an object of this invention to provide an ionization-type fire detector which overcomes the above-mentioned drawbacks of the presently-known detectors. The detector of the present invention is substantially immune to adverse effects resulting from wind currents or drafts, and this is brought about by a design of the detector in such a way that the products of combustion can readily enter therein and pass into the first above-mentioned ionized chamber, whereas rapid air currents are substantially prevented from reaching such ionization chamber. This is accomplished by providing a substantially tortuous path for external ambient air into the chamber, with such air path comprising, in part, a pair of relatively closely spaced walls which are inwardly and downwardly inclined over their length from the entry point of the device to the ionization chamber. It has been found through use of the device of the invention that this arrangement provides the desired ionization levels within the chamber and also permits the ready entry of the products of combustion into the chamber while, at the same time, considerably modifying the flow of air into the ionization chamber.

The fire detector of the present invention provides the further advantage of being attractive in appearance as compared to the prior art fire detectors and also of quite compact size. In addition, the unit is capable of being manufactured at lower cost because of its use of substantially entirely plastic parts. It has in the past been considered important to use metal parts to define the ionization chambers since electrical conductivity of the chamber walls is important; nevertheless, this obstacle is entirely overcome with the present invention by providing plastic parts and then appropriately coating selected surfaces thereof with an epoxy compound containing silver which has been found to provide high adherence under adverse environmental conditions while still providing high electrical conductivity.

BRIEF DESCRIPTION OF THE DRAWINGS

In describing the invention, reference will be made to the accompanying drawings in which.

DETAILED DESCRIPTION OF THE PREFERRED EMBODIMENT

Figure 1:
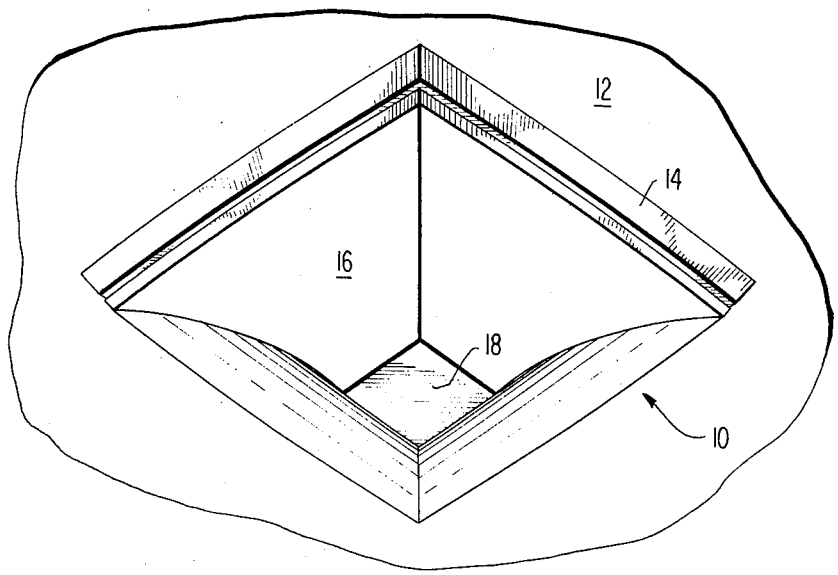
FIG. 1 is a perspective view of the exterior of the fire detector of the present invention, being viewed from the bottom and showing the fire detector as applied to a ceiling.

The fire detector of the present invention is shown in perspective view in FIG. 1. In FIG. 1, the detector 10 is shown mounted upon a ceiling 12, and it can be seen that the detector has a base portion 14 which is generally rectangular, and that from each of the four peripheral edges, there are concave inwardly extending surfaces 16 which narrow in width as they curve downwardly to a level where they join a peripheral edge of a bottom rectangular portion 18. The detector typically may be of a size such that each lateral edge at the location where the detector is fastened to the ceiling has a length of six or seven inches and with the square bottom surface 18 extending perhaps two and a half inches below the ceiling. As will subsequently be described, the majority of the individual parts which comprise the detector are formed of a plastic material which aids in providing an attractive external appearance, thereby rendering the detector less conspicuous.

Figure 2:
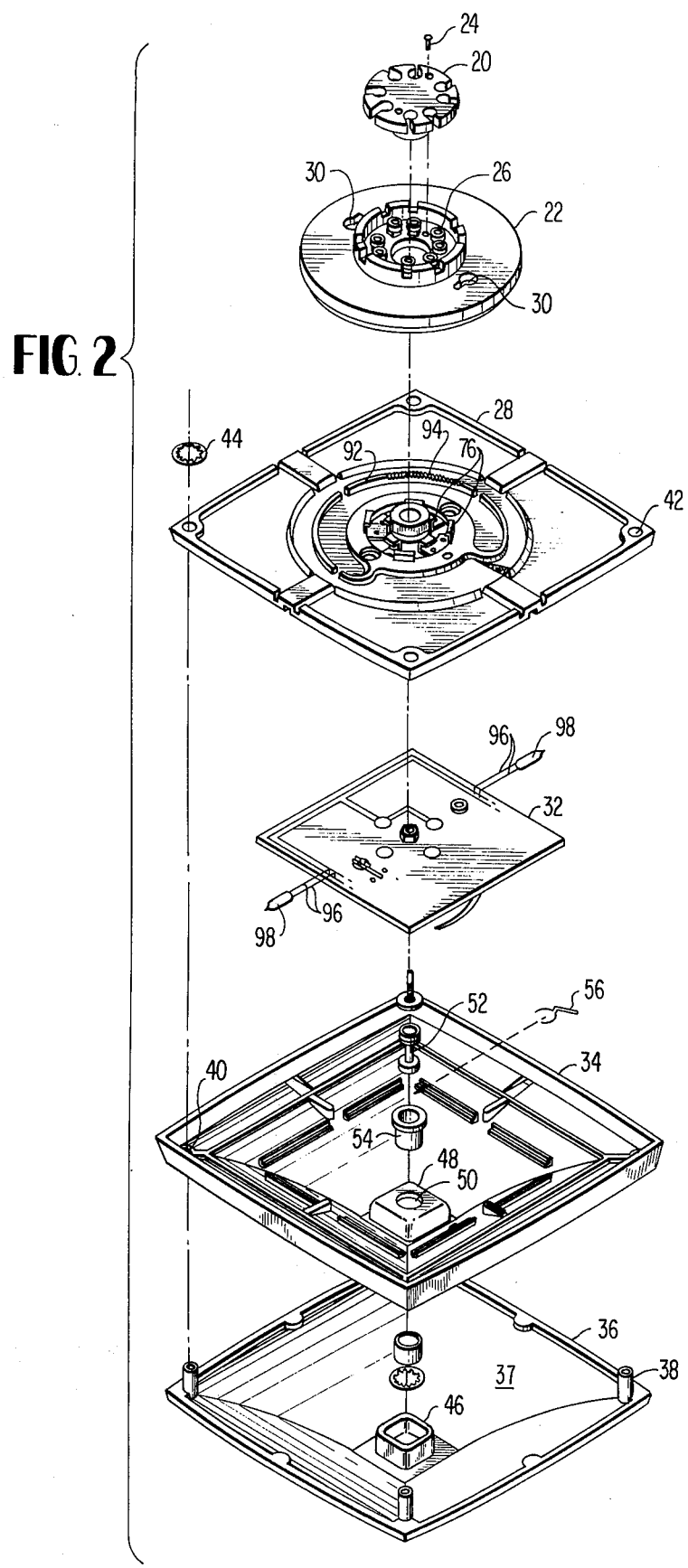
FIG. 2 is an exploded view of the various component parts of the detector of FIG. 1.

The detector of the invention is shown in exploded form in FIG. 2. The socket plate 20 and socket member 22 are assembled as a unit, and with these two parts held firmly together by a pair of rivets, one of which 24 is shown as passing through aligned apertures in the members 20 and 22. The socket plate 20 further includes a plurality of apertures for receiving connecting screws 74 (see FIG. 3) which pass through such apertures in member 20 and into metallic, electrically conductive terminal nuts 26 supported in socket 22. Each such terminal nut 26 extends through to the bottom side of socket member 22 so as to provide a means for making an electrical connection to appropriate corresponding terminals on a base member 28 as will later be more fully described.

The combination of joined elements 20 and 22 is adapted to be secured to an appropriate ceiling mounting means (not shown) which may comprise a conventional electrical junction box. As is well known, such junction box is provided with tabs for receiving an appropriate electrical fixture, and the spacing of such tabs corresponds to the spacing of the elongated slots 30 which are provided in socket 22. It will thus be readily apparent that one who is installing the fire detector unit of the present invention can quite readily secure the combination of elements 20 and 22 to such junction box by means of screws passing through the above-mentioned apertures 30 and into the threaded tabs of the junction box.

Once the above-mentioned members are secured to the junction box, the further elements disclosed in FIG. 2 may be secured thereto. Such further elements may comprise, in assembled combination, the plate 28, the circuit board 32, the inner shell 34, and the outer shell 36. It will be noted that the outer shell 36 includes a plurality of upwardly extending pins 38, one at each corner, and these extend through corresponding apertures 40 in inner shell 34 and corresponding apertures 42 in base member 28. When the several parts described above are assembled, each pin 38 extends upwardly above the respective aperture 42 in plate 28, and the parts are then held together by placing a frictional retaining ring 44 around the projecting portion of pin 38.

As can be seen in FIG. 2, the outer shell 36 defines an upstanding rectangular cavity 46, whereas the inner shell 34 defines in its bottom portion a generally rectangular cavity 48, and when the several parts are assembled as above-described, the cavity 46 fits essentially within the cavity 48, with the aperture 50 in recess 48 supporting a source holder assembly 52, a source holder 54, and a source lead 56, the latter elements cooperating to provide a source of radiation for the separate ionization chambers 103 and 104.

Figure 3:
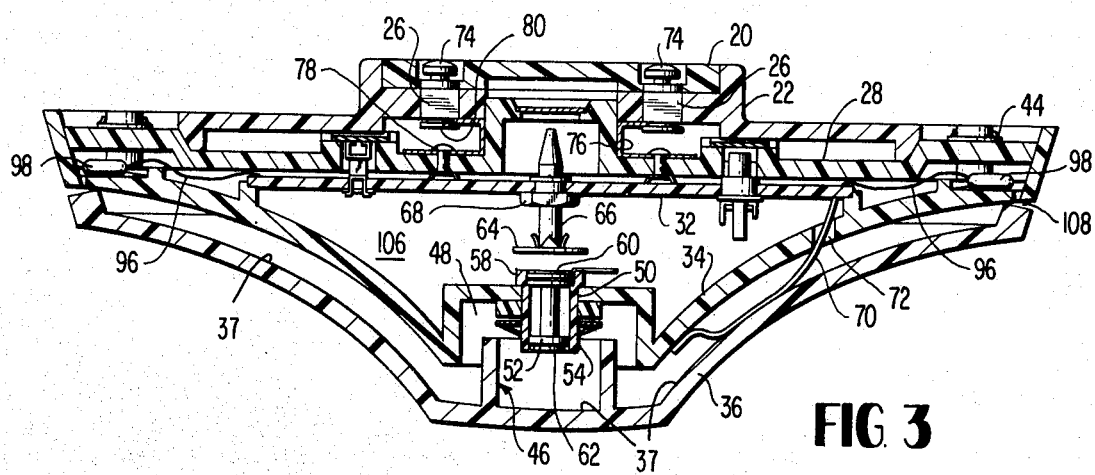
FIG. 3 is a cross-sectional view of the fire detector of FIG. 1.

Referring now to the cross-sectional view of FIG. 3, the relationship of the cavity 46 to the recess 48 is shown and also the relationship of the spaced, curved walls of the inner and outer shells 34 and 36. The aperture 50 in the inner recess 48 is shown as receiving the cylindrical source holder 54 which has a shoulder portion 58 that rests upon the upper wall of the recess. Within the Teflon source holder 54 there is supported the radiation source assembly 52 which supports at opposite ends thereof appropriate sources of radioactive material as indicated by the reference characters 60 and 62. The target plate 64 is fastened to one end of a target plate screw 66 which passes through the circuit board 32, and with clinch nut 68 being provided so that the position of the target plate 64 can be adjusted relative to radiation source 60. A flexible lead which may comprise a narrow strap of flexible copper is shown at 70 and is connected at one end to the circuit board 32, passing through an aperture 72 in inner shell 34 so as to make contact with the inner surface of outer shell 36. Such inner surface is coated with a conductive material 37 which may comprise an epoxy material impregnated with silver. Such material 37, it has been found, provides a desirable high adhesion to the inner surface of outer shell 36 while also providing good conductivity; other materials may also be used such as a graphite dispersion or a metal plating.

FIG. 3 also illustrates the socket plate 20 and socket 22 and discloses representative ones of the terminal screws 74 and nuts 26 permitting external connections to be made from the electrical junction box to which the device is physically connected to the circuit board via contact clips 76 which are secured to plate 28 by means of rivets 78. As will subsequently be described in greater detail, the contact clips 76 further provide the function of cooperating with the bottom ends of terminal nuts 26 to secure the assembly of socket plate 20 and socket 22 in a releasable manner to plate 28.

Figure 4:
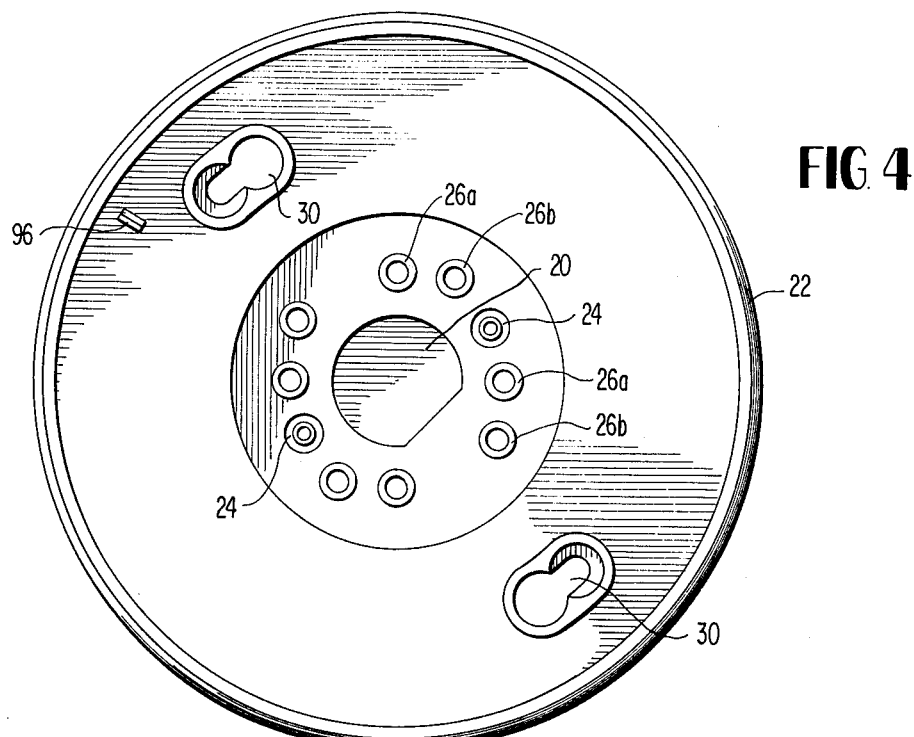
FIG. 4 is a plan view of one of the component parts of the fire detector of FIG. 2.
Figure 5:
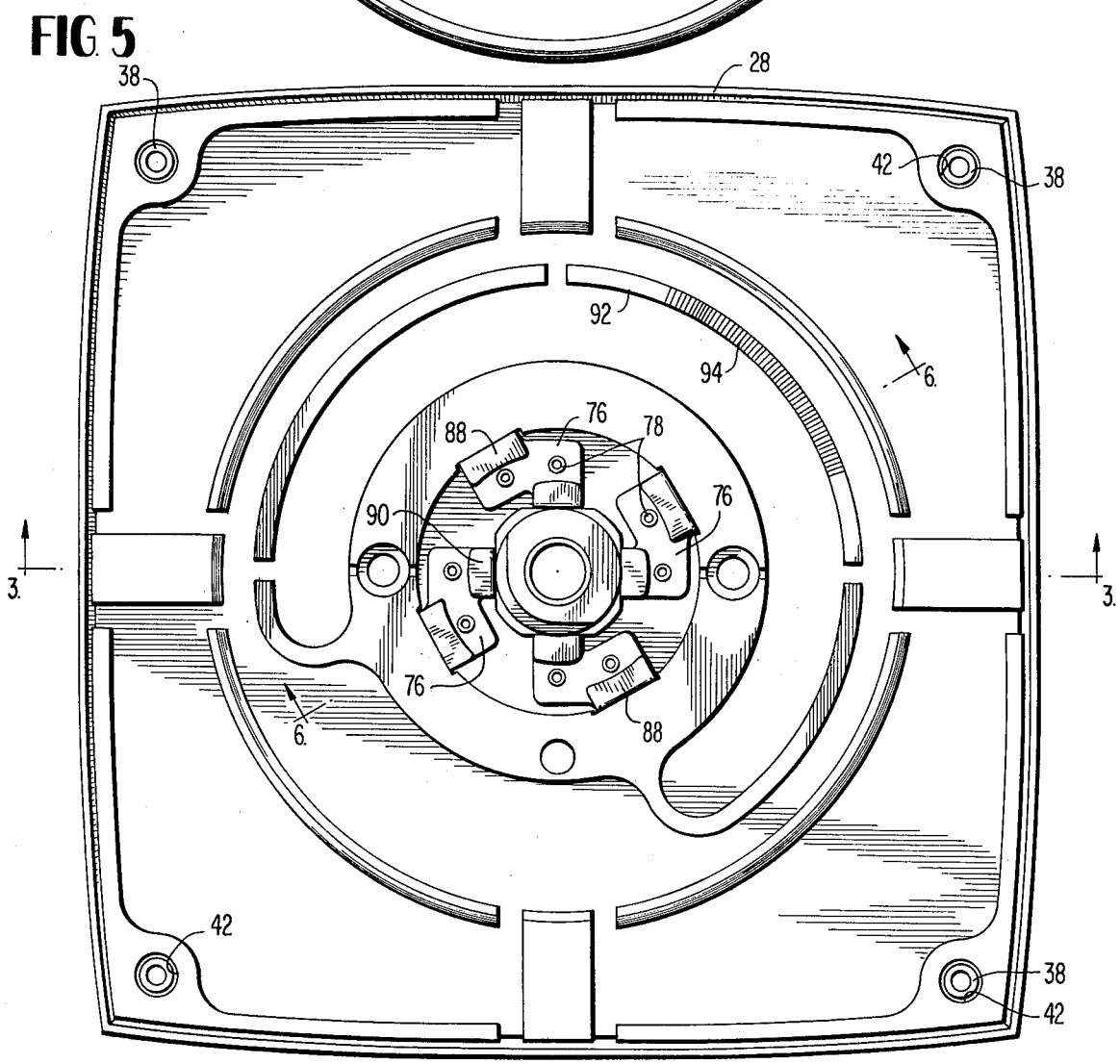
FIG. 5 is a plan view of the base element of the fire detector shown in exploded view in FIG. 2.

FIGS. 4 and 5 illustrate, respectively, the bottom surface of socket 22 as well as socket plate 20 and the top surface of plate 28. As will be seen, the respective opposing faces of these members are so configured as to provide a means whereby the plate 28 can readily be secured to an detached from the assembly of socket plate 20 and socket 22. Moreover, the arrangement is such as to permit an adjustment of the rotational position of plate 28 relative to elements 20 and 22 so as to provide for correct positioning of plate 28. Thus, in practice, when the elements 20 and 22 are secured to a conventional electrical junction box, it may of course happen that the orientation of these members 20 and 22 is such that if the plate 28 could be secured to the elements 20 and 22 in only one precise rotational position, plate 28 would then not be properly aligned with the dimensions of the room in which it was positioned. More specifically, it may be desirable from an aesthetic standpoint to position the outer shell 36, which is the only part that can ordinarily be seen by an observer, in such a way that its side edges form essentially forty-five degree angles with the side walls of the room; alternatively, it may be desirable to place the unit so that the outer shell 36 has its peripheral edges aligned with the outer walls of the room. In any event, it is highly desirable to provide a convenient means for providing a fine adjustment in position of the assemblage of elements which are to be connected to the socket plate 20 and socket 22 so that the proper aesthetic effect can be achieved even when it is not possible to provide precise alignment of the elements 20 and 22 on the electrical junction box.

Figure 6:
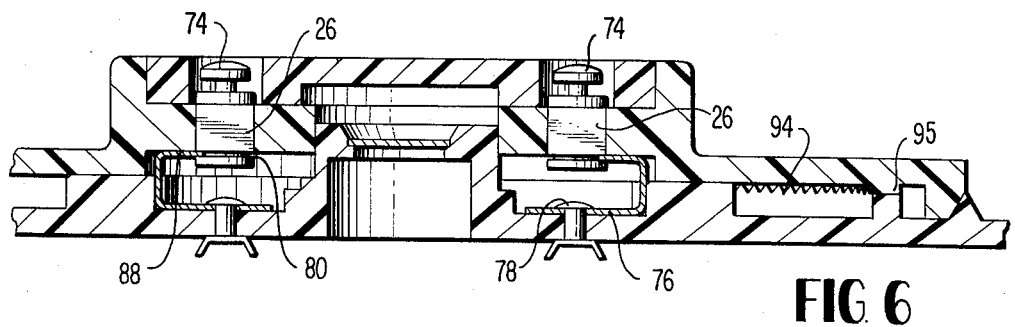
FIG. 6 is a cross-section view taken along the section line 6—6 of FIG. 5 shown with the socket of FIG. 4 installed.

FIG. 5 illustrates the four contact clips 76 which are secured by rivets 78 to the plate 28. Each such clip 76 is provided with two overhanging contact portions 88 and 90 which are in generally facing relationship with a radial spacing therebetween as well as a circumferential spacing therebetween although, as shown, they do overlap each other circumferentially. The cross-sectional view of FIG. 6 illustrates the inwardly facing contact positions 88 and shows the manner in which these engage with the grooved bottom portions 80 of terminal nuts 26.

Referring now to FIG. 4, the rivets which are used to secure the socket plate 20 to socket 22 are shown at 24. There are, in addition, four pairs of terminal nuts 26 which are spaced substantially equidistant circumferentially about the socket member 22. It will further be noted that, for each pair of socket nuts 26, a first one of these 26a is spaced radially inwardly relative to the other socket 26b of the same pair. When the plate 28 is secured to the elements 20 and 22, each pair of terminal nuts 26a and 26b engages with a respective one of the contact clips 76, the inner one 26a engaging with its grooved lower end outwardly extending contact portion 90 of contact clip 76 while the other terminal nut 26b of the pair engages with its grooved bottom end the inwardly directed portion 88 of the same contact clip 76. The arrangement of these elements is then such that the plate 28 can be placed in a selected rotational position relative to elements 20 and 22 in order to secure the desired rotational orientation of plate 28 without interfering with the proper contact between a selected one of the terminal nuts 26a, 26b of any pair with a respective one of the contact clips 76.

It will further be noted that the plate 28 defines an upstanding circular rib 92 which, over a portion of its circumference, has formed therein a plurality of circumferentially spaced notches or grooves as indicated at 94. The socket 22 has formed therein a small protuberance 95 which is so positioned that, over a predetermined range of rotation of elements 20 and 22 with respect to plate 28, the protuberance 95 will engage with the slotted or grooved portion 94 referred to above. This makes it possible to rotationally adjust the position of plate 28 relative to elements 20 and 22 while at the same time maintaining a predetermined frictional resistance to rotation. The effect is that of a ratchet so that the plate 28 can be rotated to its desired position and will be maintained in its last-adjusted position by reason of engagement of the protuberance 95 in a respective one of the grooves 94.

Figure 7:
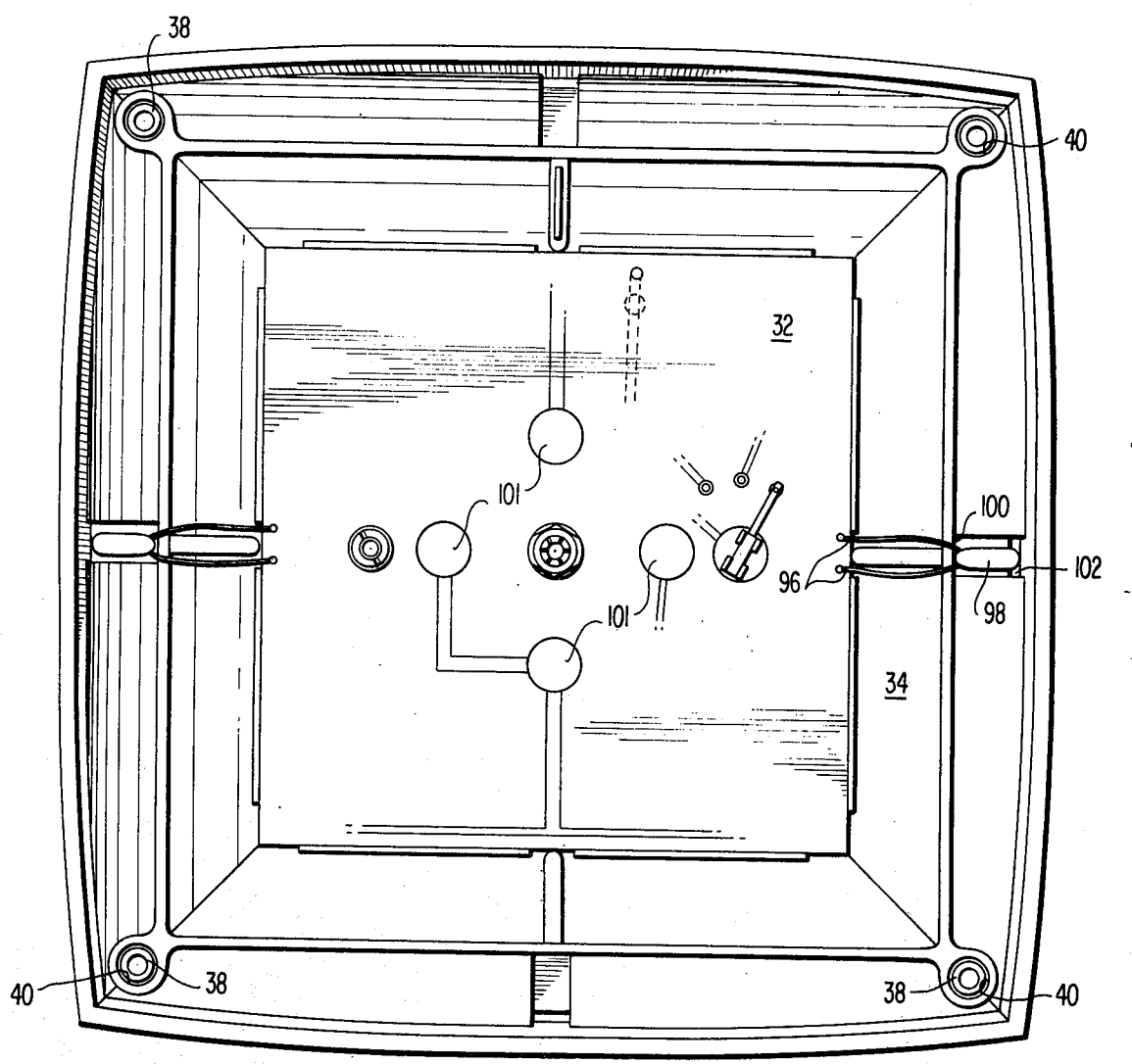
FIG. 7 is a plan view of the circuit board assembly of FIG. 2 in position on the inner shell member also shown in FIG. 2.

FIG. 7 illustrates the positioning of the circuit board 32 within a recess defined in the inner surface of inner shell 34. The circuit board is provided with two pairs of outwardly extending leads 96 on opposing sides of the circuit board, and each of these pairs of leads provides selective energization of a lamp 98 which is positioned in a recess 100 defined in the inner shell 34 adjacent its outer edges. A small slit 102 is formed in such recess 100 so as to permit illumination of the lamp 98 to be observed by an observer. As will subsequently be indicated, the existence of an alarm condition illuminates the lamps 98 thereby indicating which fire detector in the building is providing an alarm condition. This is particularly useful in those instances where a unit is falsely providing an alarm since it permits the ready determination of the faulty unit. Connections to the circuit board are made by means of rivets 78, whose lower bifurcated ends are brought into frictional contact with the input and output terminals 101 (see FIG. 7) of the circuit board 34.

Figure 8:
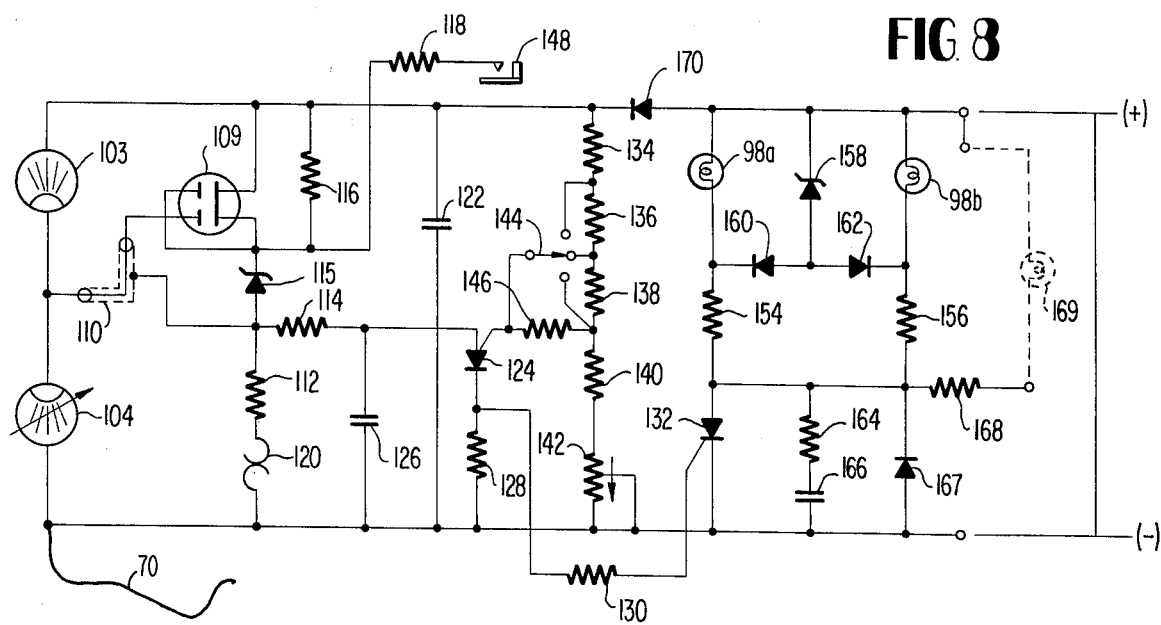
FIG. 8 is a circuit diagram of the electronic circuitry of the fire detector of this invention.

Referring now to the circuit diagram of FIG. 8, a pair of ionization chambers 103 and 104 are shown. The ion chamber 103 is a relatively closed ionization chamber and is intended to act as a reference against which the ionization of the relatively open chamber 104 is compared. Referring to the cross-sectional view of FIG. 3, the closed ionization chamber 103 is defined by the enclosed space 106 lying above the inner surface of inner shell 34 and bounded by the lower surface of circuit board 32. Within this space, the radioactive source 60 provides a source of radiation which is directed against target plate 64. The ionization chamber source 104 as represented in the circuit diagram of FIG. 8 corresponds, in the cross-section view of FIG. 3, to the space within cavity 46, the space within recess 48, and the space between the inner and outer shells 34 and 36 respectively. It is of course known in the art to provide separate ionization chambers which are connected in series and with one of the chambers being essentially isolated from aerosol products while the other is so arranged so that the aerosol products from combustion can readily enter therein. Such an arrangement is shown, for example, in the Scheidweiler et al U.S. Pat. No. 3,681,603. Such prior art patent further discloses the use of an ionization holder of generally cylindrical configuration corresponding to that which is disclosed in the present application.

It is also known in the art that the effect of the presence of aerosols in the measuring chamber is to deposit themselves upon the ions moving in the measuring chamber under the influence of an electric field. This causes a reduction of the amount of current because the mass of the aerosol particles is so many thousands of times greater than that of the ions in the ionization chamber that the ion speed of movement is rendered negligibly small in the presence of the aerosol products as compared to that when there are no aerosol products present.

It has also been recognized in the art, as mentioned particularly in the above-mentioned Scheidweiler et al patent, that in the open measuring chamber, a low-velocity of ambient air can have a significant effect on the ionization current in the detection chamber. It is quite often considered necessary, therefore, to provide some means for screening the detection chamber from moving currents of ambient air which would otherwise reduce the detection chamber currents sufficiently to provide an erroneous fire alarm signal.

With the arrangement of the present invention as shown particularly in the cross-sectional view of FIG. 3, it can be seen that ambient air can readily enter the detection chamber through the peripheral gap 108 which exists between the inner and outer shells 34 and 36. Aerosol products can readily diffuse into and throughout the detection chamber, and it has been found that they can readily migrate downward in a very short time and into the inner chamber 46 since, as is known, such aerosol products tend to distribute themselves fairly uniformly throughout the available space with the passage of time.

Although the precise reason why the physical arrangement of the present invention provides substantially improved immunity against ambient air currents is not known, it is believed to be due, at least in part, to the curved configuration of the spacing between the inner and outer shells 34 and 36. It is also believed to be due to the presence of the surrounding walls which define the cavity 46 since a flow of ambient air even into the space between the inner and outer shells 34 and 36 is substantially impeded by the walls of chamber 46 from entering the interior volume of such chamber. Moreover, although it is believed to be principally the space defined by cavities 46 and 48 that comprise the ionization chamber 104 subject to aerosols, it has also been found that this ionization chamber extends to at least a part of the curved space between the opposed surfaces of inner and outer shells 34 and 36. Thus, it has been found that the sensitivity of the detector is measurably increased by extending the conductive coating 37 over substantially the entire inner surface of outer shell 36. In any event, it has been found through extensive tests that the constructional features of the present invention permit quick and reliable detection of the presence of aerosol products while maintaining substantial immunity against false alarms resulting from wind currents in the ambient air. As is best seen in FIG. 3, the aerosol product entering through the peripheral gap 108 can reach the cavity 46 only by taking a downward direction, against the natural flow of heat convection currents, and then an upward direction. This circuitous aerosol path is believed to contribute to the improved immunity against ambient air currents.

Referring now once again to the circuit diagram of FIG. 8, as the current through the sensing chamber 104 changes as a result of the presence of aerosols, the voltage at the junction of the two chambers 103 and 104 increases. This change in voltage is sensed by the Mosfet 109. The latter device provides a high input impedance which is necessary to sense the changes in the minute ion current, and it also acts as a buffer amplifier between the ionization chambers 103 and 104 and the low impedance alarm circuitry. The gate of Mosfet 109 is connected to the junction of the ionization chambers 103 and 104 by a length of wire 110 having a Teflon shield. The conductor 110 has a small capacitance of 5 pf between the center conductor and shield. The shield of this conductor is connected as shown to the junction of resistors 112 and 114. The capacitance connected in this manner has the effect of slightly showing the response of the detector, thereby helping to eliminate false alarms due to transient effects. Also, the capacitance provided by conductor 110 limits the gate-source voltage to an acceptable level on the initial application of power.

The source electrode of Mosfet 109 follows the voltage at the ion chamber junction. The junction of resistor 112 and Zener diode 115 provides the input to the level detection portion of the circuitry.

The thermal cut-off device 120 functions as a normally closed switch which opens at a predetermined high temperature, thereby causing the detector to provide an alarm condition. The thermal cut-off is not intended to function as a fire detecting component but merely provides an indication that the unit has sustained exposure to a high temperature condition after which the unit should be returned to the manufacturer for checking and possible repair.

Capacitor 122 is provided to prevent an erroneous alarm signal which might otherwise result from electrical transients appearing on the input power lines.

Level detection of the input is provided through the use of a programmable unijunction transistor 124. It is a characteristic of such a device that its anode-cathode junction presents a high impedance to current flow until the anode electrode becomes positively biased with respect to the gate electrode. At this time, the device functions as a regenerative loop, and the effect is the same as shorting together all three electrodes. When this occurs, capacitor 126 discharges through resistor 128 in parallel with resistor 130 which is in series with the gate-cathode junction of SCR 132.

The voltage divider comprising series-connected resistors 134, 136, 138, 140 and potentiometer 142 provide a reference voltage for the gate of transistor 124. By shorting out either resistor 138, or the series combination of resistors 136 and 138, with switch 144, the voltage at the gate of transistor 124 may be changed, thereby increasing or decreasing the voltage swing needed to be provided by Mosfet 108 to produce a regenerative effect with respect to transistor 124. In this manner, the sensitivity of the unit may be adjusted.

Potentiometer 142 comprises a factory-set potentiometer which is used to adjust for the variation in gate-source bias characteristics of the Mosfet 109. Resistor 146 functions as a safety device in the event that switch 144 should become open circuited. If this were to happen, the voltage at the gate of transistor 124 would automatically assume a level which would cause the unit to operate in its most sensitive condition.

The sensitivity of the unit in response to the presence of smoke may be monitored by observing the source voltage of Mosfet 109. A monitoring jack 148 provides access to this point in the circuit through a resistor 118 which is connected in series with the jack 148 to prevent damage due to accidental shorting of this point to ground.

When transistor 124 fires in the manner previously described, current passes through resistor 130 and through the gate electrode of SCR 132. This causes SCR 132 to turn on and current then passes through the lamps 98a, 98b and through dropping resistors 154, 156. The illumination of lamps 98a, 98b provides a visual indication at the location of the detector unit that the particular unit has responded to the presence of aerosols. A remote indication lamp 169 may be connected as shown to provide an indication at a monitoring station of the triggering of the unit to signal a fire alarm. Zener diode 158 provides alarm current should either or both of the lamps burn out. Diodes 160 and 162 provide a steering function.

Resistor 164 and series capacitor 166 have the effect of damping rapid rates of voltage rise across SCR 132, thereby tending to prevent spurious triggering. Diode 167 provides a current path to light the lamps 96a and 96b should the polarity of the wiring be reversed. This feature immediately alerts the installer to the fact that the wiring has been inadvertently crossed. Resistor 168 comprises a dropping resistor in the event that an external lamp 169 is to be connected to the unit. Diode 170 is provided in series with the input power leads to prevent damage to the sensing and level detection circuitry in the event of polarity reversal of the input leads.

What we claim is:

1. In a ceiling-mounted ionization type fire detector having at least one ionization chamber which is open to the entrance of aerosols but is protected against the effect of ambient air currents comprising:
    an inner shell member and an outer shell member,
    the outer surface of said inner shell member and the inner surface of said outer shell having generally similar geometric shapes and being supported in superimposed generally parallel spaced relationship to each other and with said inner shell closer to the ceiling than said outer shell,
    said inner and outer shell members both having their opposing surfaces inclined inwardly and downwardly over a substantial portion thereof from their substantially common peripheral spaced edges adjacent the ceiling towards their central portions which are more distantly spaced from the ceiling,
    said inner and outer shells defining at their said common edges an aperture for the passage of aerosols, but with said outer shell being otherwise substantially imperforate,
    a chamber formed between said inner and outer shells substantially at their center and having a surrounding wall,
    means for ionizing the air in said chamber,
    and means responsive to the change in electrical conductivity in said chamber in the presence of aerosols for providing an alarm signal.

2. The apparatus of claim 1 in which said inner and outer shells both have a rectangular outer periphery.

3. The apparatus of claim 2 wherein said inner shell comprises means for supporting said ionizing means.

4. The apparatus of claim 2 wherein said inner and outer shells each define a central rectangular planar portion lying in a plane below that of their outer peripheral, each peripheral edge of each said shell being joined with a respective edge of said planar portion by a concave curved portion.

5. The apparatus of claim 1 wherein said inner and outer shells are both dished downwardly relative to their peripheral portions which both lie closely adjacent the ceiling when said detector is mounted on the ceiling, said inner shell defining above its upper surface a second substantially enclosed ionization chamber.

6. The apparatus of claim 1 which further includes a socket member adapted for connection to a ceiling, and means for mounting said inner and outer shells to said socket member, said mounting means permitting the rotational adjustment of said shells relative to said socket member.

7. The apparatus of claim 1 in which said inner and outer shells are plastic.

8. The apparatus of claim 7 wherein the inner surface of said outer shell supports a coating of an electrically conductive material.

9. The apparatus of claim 8 wherein said material comprises a silver impregnated epoxy resin.

10. The apparatus of claim 2 wherein said inner shell supports a printed circuit board, said inner shell and said circuit board enclosing a volume which forms a second ionized chamber, an aperture in said inner shell, an electrically conductive coating on the inner surface of said outer shell, and conductor means electrically connecting said circuit board to said conductive coating and passing through said aperture.

11. An ionization type fire detector for use in an enclosed space such as a room or the like having at least one ionization chamber which is open to the entrance of aerosols but is protected against the effect of ambient air currents comprising:
  a first shell adapted for mounting adjacent the ceiling of the room,
  means including said first shell for defining air inlet means around the periphery of said shell closely adjacent said ceiling, said first shell being otherwise substantially imperforate,
  and means defining said ionization chamber within the space between said first shell and the ceiling and below the level of said air inlet means,
  means including said first shell defining an air passageway extending from said air inlet means to said ionization chamber to permit aerosols and air currents to readily penetrate within said first shell but to reach said ionization chamber only by moving downwardly from said air inlet means to said downwardly disposed chamber.

12. The apparatus of claim 11 wherein said air inlet means comprises a peripheral slit.

13. The apparatus of claim 11 which further includes a second shell detachably connected to said first shell and between said first shell and the ceiling said second shell being closely spaced from said first shell, means including said first and second shells for defining downwardly and inwardly inclined passages from said air inlet means to said ionized chamber.

14. The apparatus of claim 13 wherein said inner shell defines a second enclosed ionized chamber which is substantially isolated from ambient air.

15. The apparatus of claim 11 which further includes barrier means surrounding said first-named ionized chamber for impeding the flow of air entering said air inlet means and traveling downwardly and inwardly along the inner surface of said outer shell.

16. The apparatus of claim 15 wherein said barrier means is at least in part integral with said outer shell.

* * * * *